United States Patent [19]
Klingenbeck et al.

[11] Patent Number: 4,798,209

[45] Date of Patent: Jan. 17, 1989

[54] METHOD AND APPARATUS FOR NON-CONTACTING IDENTIFICATION OF THE TEMPERATURE DISTRIBUTION IN AN EXAMINATION SUBJECT

[75] Inventors: Klaus Klingenbeck, Hessdorf; Rudolf Schittenhelm, Erlangen, both of Fed. Rep. of Germany

[73] Assignee: Siemens Aktiengesellschaft, Berlin and Munich, Fed. Rep. of Germany

[21] Appl. No.: 1,980

[22] Filed: Jan. 9, 1987

[30] Foreign Application Priority Data

Jan. 23, 1986 [DE] Fed. Rep. of Germany ....... 3601983

[51] Int. Cl.⁴ .............................................. A61B 5/05
[52] U.S. Cl. .................... 128/653; 128/804; 128/399; 128/736
[58] Field of Search ............... 128/653, 804, 399, 736; 374/122

[56] References Cited

U.S. PATENT DOCUMENTS

| | | | |
|---|---|---|---|
| 4,416,552 | 11/1983 | Hessemer, Jr. et al. | 374/122 |
| 4,583,869 | 4/1986 | Chive et al. | 128/653 |
| 4,641,659 | 2/1987 | Sepponen | 128/653 |
| 4,669,475 | 6/1987 | Turner | 128/736 |
| 4,677,988 | 7/1987 | Constant et al. | 128/736 |

FOREIGN PATENT DOCUMENTS 2000335 6/1970 United Kingdom .

OTHER PUBLICATIONS

"Applications de la Radiometrie Microonde en Genie Biomedical," Leroy et al., L'Onde Electrique, Jan.-Feb. 1985, vol. 65, No. 1, pp. 9–15.

"Inversion of Radiometric Data from Biological Tissue by an Optimisation Method," Schaller, Electronic Letters Apr. 26, 1984, vol. 20, No. 9, pp. 380–382.

"Aperture Syntheses Thermography—A New Approach to Passive Microwave Temperature Measurements in the Body," Haslem et al., IEEE Trans. on Microw. Theory & Tech., vol. MTT-32, No. 8, Aug. 1984, pp. 829–834.

Primary Examiner—Francis J. Jaworski
Assistant Examiner—George Manuel
Attorney, Agent, or Firm—Hill, Van Santen, Steadman & Simpson

[57] ABSTRACT

A method and apparatus for undertaking a non-contacting measurement of the three-dimensional temperature distribution in a non-uniform examination subject direct microwave radiation at the examination subject, detect the three-dimensional phase and amplitude of microwave radiation which is attenuated and scattered by the examination subject, and calculate the three-dimensional dielectric constant distribution in the examination subject on the bases of the detected phase and amplitude values. In a separate step the characteristic thermal radiation of object is measured, too. The three-dimensional temperature distribution of the examination subject is then calculated from both the three-dimensional dielectric constant distribution data and the characteristic thermal readiation data of a selected location.

23 Claims, 1 Drawing Sheet

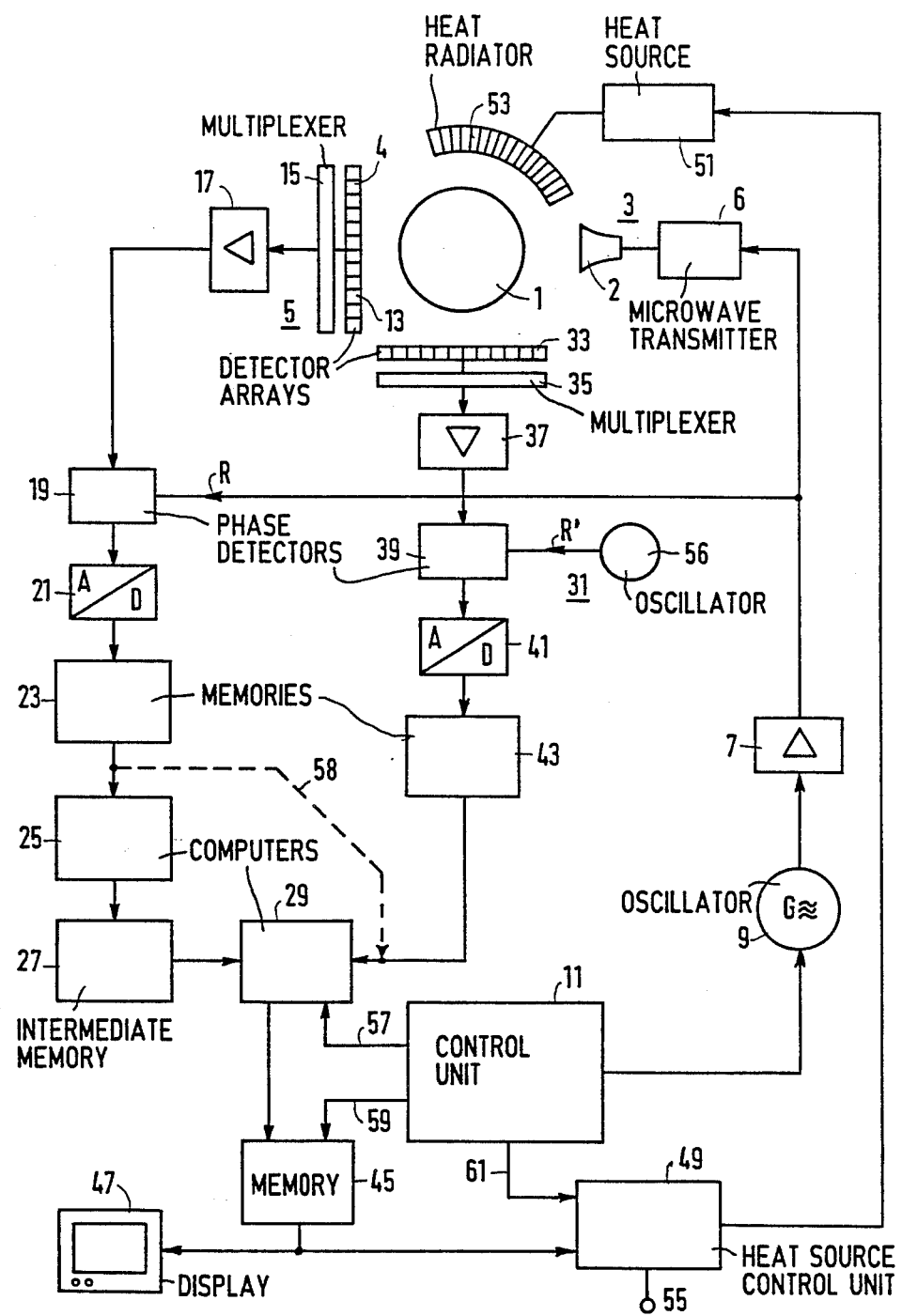

4,798,209

METHOD AND APPARATUS FOR NON-CONTACTING IDENTIFICATION OF THE TEMPERATURE DISTRIBUTION IN AN EXAMINATION SUBJECT

BACKGROUND OF THE INVENTION

1. Field of the Invention

The present invention relates to a method and apparatus for non-contacting identification of the temperature distribution in a non-uniform examination subject which may use of phase and amplitude measurements of attenuated microwave radiation directed at the examination subject.

2. Description of the Prior Art

The temperature distribution of an examination subject is of particular interest in the medical field, wherein the examination subject is a human patient. It is possible to analyze the temperature distribution of a patient to identify areas exhibiting a pathological condition because diseased tissue exhibits a different heat dissipation from healthy tissue. It is also possible using a hyperthermia method to undertake local heating of an area affected by a nidus, for example, a tumor, in order to achieve decomposition of diseased cells, particularly in combination with radiation therapy. Under such treatment methods, the heating cannot exceed a critical limit value, and must be topically within the diseased area so that no healthy tissue is damaged. In a hyperthermia method, the temperature distribution is also of interest to assist in precisely localizing the area of heat application, and monitoring the success of the therapeutic measures.

As a consequence of the slight temperature differences which occur in the human body, methods for identifying the temperature distribution in humans must do so with a high precision. This requirement is difficult to meet, however, because, given a dielectrically non-uniform examination subject, such as the human body, the distribution of the complex dielectric constant in the examination subject enters significantly into the measured result, not only for measuring the characteristic radiation of the subject, but also measuring the actual temperature.

In the human body, for example, the dielectric constant varies between a value $\epsilon = 10$ for fat tissue up to a value $\epsilon = 60$ for bone. Because of the different dielectric constants, the characteristic radiation which emanates from a point in the examination subject is differently attenuated and refracted in the tissue, so that it is not possible to obtain an unambiguous result outside of the examination subject. Given the same temperature, a region within the examination subject having a high dielectric constant radiates more strongly than a region having a low dielectric constant. The intensity of the characteristic region outside of the examination subject is thus a function of the distribution of the dielectric constant and of the temperature. Making the assumption that the dielectric constant corresponds, for example, to an average value, causes incorrect results. For example, it is possible that a first area in the examination subject measured at 40° C. on the basis of the characteristic radiation is in reality colder that a second area measured at 37° C. If the first area measured at 40° C. has an extremely high dielectric constant, its characteristic radiation in comparison to the area measured at 37° C. will be incorrectly evaluated, the latter area having a low dielectric constant in accordance with the assumption.

A method and apparatus of the type described above are disclosed in the article "Aperture Synthesis Thermography:" Haslam et al, IEEE Transactions on Microwaves, Vol. MTT-32, No. 8, August 1984. The characteristic thermal radiation of an examination subject in this method and apparatus is received by an antenna. The received signal is divided in terms of amplitude and phase in a computer, these values serving for calculating the temperature distribution. The complex relationship with the dielectric constant and the problems resulting therefrom with respect to the reliability of the measured results are not discussed in detail in this publication.

SUMMARY OF THE INVENTION

It is an object of the present invention to provide a method and apparatus for non-contacting identification of the temperature distribution in a non-uniform examination subject which permits the temperature distribution to be identified with high precision.

The above object is achieved in accordance with the principles of the present invention wherein a three-dimensional distribution of the complex dielectric constant is measured in the examination subject and this three-dimensional distibution of the complex dielectric constant is then taken into consideration in a second step for deriving the temperature distribution. In this manner, the temperature distribution is identified taking the non-uniform attenuation and scatter of the characteristic thermal radiation into consideration.

An apparatus for practicing the above method has a microwave transmitter and a microwave receiver, which may be in the form of a single detector or first and second detectors. If two detectors are utilized, a first microwave detector is connected to an evaluation circuit which identifies the three-dimensional distribution of the dielectric constant in the examination subject and supplies information regarding this distribution to the first input of a calculating means. The second microwave detector is used to acquire the characteristic thermal radiation of the examination subject, and information regarding this characteristic thermal radiation is supplied to the second input of the calculating means in terms of magnitude and phase. A signal representing the three-dimensional temperature distribution in the examination subject is then obtained at the output of the calculating means.

In an embodiment using only one microwave detector, the detector is connected to both evaluation circuits and is switched therebetween.

By obtaining the three-dimensional distribution of the dielectric constant in the examination subject, and taking this distribution into consideration in calculating the three-dimensional temperature distribution, it is assured that the characteristic radiation emitted from an area within the examination subject is processed with the weighting appropriate thereto. On the basis of the measured distribution of the dielectric constant, the attenuation and scatter of the characteristic radiation in the non-uniform examination subject is incorporated into the final calculation, so that the characteristic thermal radiation measured outside of the examination subject is corrected in accordance with its path through the examination subject. The correction is undertaken with reference to the distribution of the dielectric constant present along the propagation path between the subject area of interst and the reception means. The method and apparatus thus enable even minute temperature differences to be identified with high three-dimensional resolution in a non-uniform examination subject.

In a further embodiment of the invention, a heating source is provided for heating a prescribed volume in the examination subject.

If the examination subject is a patent and the prescribed volume is a diseases area of the patient, the heating source can be utilized under control of the measurement apparatus so that only the diseased area, for example, an ulcer or cancer cells, is elevated in temperature and a high destruction rate of the diseased cells is achieved. For effective tumor treatment, the temperature in the tumor and in the surrounding normal tissue, should be brought as close as possible to the maximum temperature of 42° through 43° C. which is permitted for the normal tissue. During this hyperthermia in the prescribed volume, temperature supervision with a precision of fractions of one degree Celsius and with a three-dimensional resolution of at least one centimeter is required. Such precise temperature supervision can be achieved with the method and apparatus disclosed herein.

DESCRIPTION OF THE DRAWINGS

The single FIGURE is a schematic block diagram for an apparatus for undertaking a non-contacting identification of the three-dimensional temperature distribution in an examination subject, which practices the method described herein.

DESCRIPTION OF THE PREFERRED EMBODIMENTS

An examination subject schematically represented at 1, such as a human body, is disposed between a radiator 2 of a microwave transmitter 3 and the reception antenna 4 of a first microwave reception means 5. For better coupling, the intervening space between the radiator 2, the subject 1 and the reception antenna 4 may be occupied by a coupling medium. The transmission frequency of the microwave transmitter 3 may be at a value in the range from about 0.1 through about 10 GHz. A range between about 1 and about 3 GHz is preferable. The microwave transmitter 3 also includes a transmission amplifier 7 and an HF oscillator 9 connected to a control unit 11. The transmission amplifier 7 may be adjusted such that a power of about 10 mW per square centimeter is available at the examination subject 1. The HF oscillator 9 operates with a fixed frequency which is adjustable. The adjusted frequency corresponds to that frequency which is desired at the microwave transmitter 3. The HF oscillator 9 receives start and stop instructions from the control unit 11. Operation of the microwave transmitter 3 is controlled by the control unit 11 in this manner.

A first microwave reception means 5 includes the reception antenna 4 which may, for example, be a two-dimensional array, a first multiplexer 15, a first reception amplifier 17, a first phase detector 19, a first analog-to-digital converter 21, and a first memory 23. In accord with a control signal, the first multiplexer 15 connects a selected reception element 13 of the reception antenna 4 to the first reception amplifier 17. The received signal amplified in the first amplifier 17 is divided in terms of amplitude and phase in the first phase detector 19. For that purpose, the first detector 19 is supplied with a reference signal R taken from the output of the transmission amplifier 7. The amplitude and phase are each converted into a digital signal in the first analog-to-digital converter 21 and are entered into the first memory 23 true to position.

The output of the first memory 23 is connected to a computer 25 which calculates the distribution of the dielectric constant in the examination subject 1 from the stored amplitude and phase data of the received microwave signals. This three-dimensional distribution is stored in an intermediate memory 27. The output of the intermediate memory 27 is connected to a first input of a further computer or calculating means 29.

The control unit 11 activates the microwave transmitter 3 by the aforementioned start instructions. The examination subject 1 is irradiated in accordance with the preselected transmission frequency in the microwave range. The radiation is attenuated and scattered in the examination subject 1, and the transmitted radiation is detected by the first microwave reception means 5. The reception signals of the reception means 5, in terms of amplitude and phase, are supplied to an evaluation circuit consisting of the computer 25 and the intermediate memory 27 wherein the three-dimensional distribution of the dielectric constant is the examination subject 1 is identified.

A method and apparatus for identifying the three-dimensional distribution of the dielectric constant are described in German OS No. 35,31,893, corresponding to copending U.S. application Ser. No. 903,999, filed Sept. 4, 1986. The method disclosed therein is suitable for use as one step in the method disclosed herein.

As described in the aforementioned German OS No. 35 31 893 and U.S. application Ser. No. 903,999, the three-dimensional distribution of dielectric constants in an object such as a patient can be accomplished by emitting radiation directed at the object, receiving radiation which is transmitted and scattered by the object in a selected volume, measuring the amplitude and phase of the received radiation, calculating the three-dimensional distribution of the dielectric constants in the object from the amplitude and phase of the received radiation in the selected volume, and, if desired, visually displaying the result of the calculation. The following equations can be used to calculate the three-dimensional distribution of the dielectric constants:

$$V(r) = \omega/c(\sqrt{\epsilon\mu} - \sqrt{\epsilon(r)\cdot\mu(r)}$$

and $$V = G_S^-\psi_S(1 \cdot \psi_o + G_S G_T^{-1}\psi_S)^{-1},$$

wherein $V(r)$ is the scatter potential, $\omega = 2\pi f$ is the radian frequency for the emitted radiation, c is the speed of light, $\epsilon$ is the dielectric constant of any radiation coupling medium, surrounding said object, $\mu$ is the permeability of said coupling medium $\mu(r)$ is the permeability of the object, $G_S$ is the Green's function for propagation of the radiation from the object to a measuring location within the selected volume, $G_T$ is the Green's function for propagation of radiation between two locations in the object, $G_S^{-1}$ is the inverted Green's function $G_S$, $\psi_o$ is the incoming radiation field at the object, $\psi_S$ is the scatter field at the measuring location, 1 1 is a unit operator, and $\epsilon(r)$ is the distribution of dielectric constants in the object.

A second microwave reception means 31 is also directed at the examination subject 1. The second microwave reception means 31 includes a second reception antenna 33, which may also be in the form of a two-dimensional array, a second multiplexer 35, a second reception amplifier 37, a second phase detector 39 supplied with a reference signal R' from another oscillator 56, a second analog-to-digital converter 41, and a second memory 43. The output of the second analog-to-digital converter 41 is supplied to the second memory 43, which has an output connected to a second input of the calculating means 29. The manner of functioning of the second reception means 31 is analogous to that of the first reception means 5. Allocated to the reception location, the received microwave signals, divided in terms of amplitude and phase, are available at the output of the second memory 43. The reception antenna 33 is disposed at a right angle relative to the emission direction of the radiator 2.

With the assistance of the microwave transmitter 3 and the first reception means 5 the distribution of the dielectric constant in the examination subject 1 is identified in accordance with the teachings of aforementioned copending application Ser. No. 903,999. If the temperature distribution in the examination subject 1 exhibits only extremely small differences and is chronologically constant, the distribution of the dielectric constant $\epsilon$ remains substantially unaltered over the entire examination timespan. In such a case, the characteristic radiation is preferably measured by the second microwave reception means 31 with an inactivated microwave transmitter 3, because a renewed measurement of the distribution of the dielectric constant $\epsilon$ is not necessary. The first and second reception means 5 and 31 need not be simultaneously operated. It is also possible to tune the reception amplifiers 17 and 37 to the same frequency of, for example, 3 GHz.

If the examination is undertaken in conjunction with a hyperthermia treatment, i.e., heating at a prescribed temperature within the examination subject 1, and if a modification in the distribution of the dielectric constant $\epsilon$ in the examination subject 1 is anticipated, measurement of the distribution of the dielectric constant $\epsilon$ must be undertaken again during the examination timespan. If this is to be undertaken in parallel with identification of the characteristic radiation of the examination subject 1, the first and second reception amplifiers 17 and 37 are preferably tuned to different frequencies. The first reception amplifier 17 may be tuned to a transmission frequency of the microwave transmitter 3 of, for example, 3 GHz, and the second reception amplifier may be tuned to a frequency of, for example, 1 GHz. Errors in the identification of the characteristic radiation of the examination subject 1 due to the microwave radiation attenuated in the examination subject 1 can be suppressed in this manner. A reference signal R' of the phase detector 39 is then a fixed reference signal having the same frequency of 1 GHz.

The calculating means 29 has an output at which the three-dimensional temperature distribution in the examination subject 1 is available after the calculation has been completed. The algorithm which is used in the calculating means 29 will be discussed in detail below. The output of the calculating means 29 is connected to a further memory 45 for storing the three-dimensional temperature distribution. The output of the memory 45 is connected to a display unit 47. The display unit 47 may, for example, be a picture screen on which the temperature distribution of desired planes or slices in the examination subject 1 can be displayed. The output of the memory 47 is also connected to a heat source control unit 49, which operates a heating source 51 including a heat radiator 53. The heat radiator 53 is directed at the examination subject 1, and can heat a prescribed volume therein.

The heat radiator 53 may be any suitably shaped baffle or other means for locally directing heated air from the heat source 51 toward the examination subject 1.

The heat source control unit 49 identifies the temperature maximum in the three-dimensional temperature distribution in the examination subject 1. In the temperature maximum exceeds a prescribed limit value, the heating source 51 will be disconnected by the control unit 49. For a human patient as the examination subject 1, this prescribed limit value is approximately 43° C.

The coordinates in the examination subject 1 identifying the location at which the temperature maximum exists are also identified in the control unit 49. These coordinates are compared to prescribed coordinates of a volume in the examination subject 1 which are entered into the control unit 49 via an input 55. The prescribed coordinates may, for example, have been identified with the assistance of computer tomography or NMR exposure, and may be the coordinates, for example, of the center of a tumor. Dependent upon a comparison of the prescribed coordinates to those for the identified temperature maximum, the control unit 49 automatically guides the emission direction of the heat radiator 53 such that the coordinates of the maximum of the temperature distribution coincide with the prescribed coordinates, i.e., with the center of the tumor. It is assured in this manner that the temperature maximum, given treatment using a hyperthermia method, will be accurately subjected to heat for destroying the diseased tissue. The calculating means 29, the memory 45 and the heat source control unit 49 are all controlled by the main control unit 11 by respective control lines 57, 59 and 61.

In a further embodiment, the first and second microwave reception means 5 and 31 can be combined to form a common reception means. For example, only the components of the reception means 5 need then be provided from the antenna 4 through the memory 23. The reception means 5 then serves both for identifying the distribution of the dielectric constant $\epsilon$ and for identifying the characteristic radiation of the examination subject 1. In this embodiment, it is necessary that the microwave transmitter 3 be disconnected when the characteristic radiation of the examination subject 1 is identified. This operating mode is undertaken by the control unit 11. In this embodiment, a connection 58, indicated by dashed lines, runs from the output of the memory 23 to the second input of the calculating means 29. The amplitude and phase of the characteristic thermal radiation are thus supplied to the calculating means 29 ia this connection 67.

In this embodiment, only that which is referred to as "off line" operation is possible. This means that identification of the temperature distribution from the dielectric constant and identification of the characteristic thermal radiation ensue subsequently rather than simultaneously.

That which is referred to as "on line" operation, by contrast, is possible by using the two microwave reception means 4 and 31. As described above, the two reception amplifiers 17 and 37 are tuned to different frequencies, of, for example, 3 and 1 GHz respectively, for this type of operation. The intermediate memory 27 may be omitted when the apparatus is operated in this manner. The output of the computer 25 is then directly connected to the first input of the calculating means 29. The calculating means 29 thus respectively simultaneously receives at its two inputs the value of the dielectric constant $\epsilon$ the value of the amplitude and phase of the characteristic thermal radiation for a three-dimensional point in the examination subject 1. The calculating means 29 can identify the temperature T at that location from this information.

The following intergral equation is solved in the calculating means 29:

$$S(\underline{r}) \propto \int d^3 r' \epsilon(\underline{r}') T(\underline{r}') G(\underline{r}-\underline{r}') \tag{1}$$

In the above equation, $S(\underline{r})$ denotes the characteristic thermal radiation of the examination subject 1 at a location $\underline{r}$. The characteristic radiation $S(\underline{r})$ is known on the basis of the amplitude and phase of the microwave radiation incident on the antenna 33. The functions $\epsilon(\underline{r}')$ is the distribution of the dielectric constant in the examination subject 1. This is identified, for example, in accordance with the aforementioned U.S. Application Ser. No. 903,999, and is supplied to the first input of the calculating means 29, either from the memory 27 or directly from the computer 25. The function $T(\underline{r}')$ is the desired temperature distribution for which the above integral equation (1) is to be solved. The function $G(\underline{r}-\underline{r}')$ is Green's function, which describes the propagation of the microwave radiation from the location $\underline{r}'$ of a point in the examination subject 1 to the location $\underline{r}$ of a point in the reception antenna 33. The terms r and $\underline{r}'$ are thus location vectors respectively from a point of origin to the reception antenna 33 or to the examination subject 1.

Green's function $G(\underline{r})$ is defined by the integral equation (2):

$$G(\underline{r}) = G_o(\underline{r}) + \int d^3 r' G_o(\underline{r}-\underline{r}') \cdot (k_o^2 - k^2(\underline{r}')) \cdot G(\underline{r}') \tag{2}$$

wherein in $G_o$ is Green's function for the propagation of microwave radiation in the surrounding coupling medium. $G_o$ is defined by the following differential equation (3):

$$(\Delta + k^2) G_o(\underline{r}-\underline{r}') = \partial(\underline{r}-\underline{r}') \tag{3}$$

In the above equation $k_o$ is the wave number of the microwave radiation in the coupling medium, and $k(r)$ is the wave number of the microwave radiation in the examination subject 1. $k_o = \omega/c \cdot \sqrt{\epsilon_o \mu_o}$, and $k(\underline{r}) = \omega/c \sqrt{\epsilon(r)\mu(r)}$, wherein $\epsilon_o$ and $\mu_o$ are respectively the dielectric constant and permeability of the coupling medium, and $\epsilon(\underline{r})$ and $\mu(\underline{r})$ identify the three-dimensional distribution of the corresponding quantities in the examination subject 1. $\Delta$ is the Laplacian differential operator $$\Delta = \frac{\partial^2}{\partial x^2} + \frac{\partial^2}{\partial y^2} + \frac{\partial^2}{\partial z^2}$$

the function and the $\partial(\underline{r}-\underline{r}')$ is the Dirac $\partial$-function. The analytic form of $G_o$ are the known speherical waves $$G_o(r-r') = \sqrt{\frac{1}{4\pi}} \cdot \frac{e^{ik_o|r-r'|}}{|r-r'|} \tag{4}$$

the value $\omega$ is the radian frequency of the microwave radiation and c is the speed of light. When $\epsilon(r)$ or $\epsilon(r) \cdot \mu(r)$ are known from the microwave imaging, the required Green's function G can be calculated from the above integral equation (2). Because the integral equation (2) for G contains the non-uniform distribution of the dielectric constants of the examination subject, G(r) describes the propagation of the radiation from a point in the examination subject to the detector taking the attenuation and scatter in the examination subject into consideration.

Integral equation (1) is solved by transformation into Fourier space, by the following relationship, wherein * denotes the Fourier convolution: $(\epsilon * T)(\underline{k}) \cdot G(\underline{k}) \alpha S(\underline{k})$ (5) and $$(\epsilon * T)(\underline{k}) \propto \frac{S(\underline{k})}{G(\underline{k})} = R(\underline{k}) \tag{6}$$

In the above, k is the three-dimensional spatial frequency vector. After back-transformation into the local space by inverse Fourier transformation, equation (6) can be rewritten as:

$$\epsilon(\underline{r}) \cdot T(\underline{r}) \propto FT^{-1}[(S/G)] = R(\underline{r}) \tag{7}$$

Wherein $FT^{-1}$ denotes the inverse Fourier transformation. The temperature distribution $T(\underline{r})$ can be identified therefrom in accord with the following equation:

$$T(r) = \frac{1}{\epsilon(\underline{r})} \cdot R(\underline{r}) \tag{8}$$

The method for identification of the temperature distribution $T(\underline{r})$ in the examination subject 1 is undertaken in the following sequence. The microwave transmitter 3 is activated and emits microwaves in a direction toward the examination subject 1. These mirowaves are three-dimensionally attenuated and scattered to differing degrees in the non-uniform examination subject 1. The microwave radiation energing from the examination subject 1 is acquired by the first reception means 5 and is divided in terms of amplitude and phase. The distribution of the dielectric constant $\epsilon(\underline{r})$ is calculated in the computer 25 and is stored in the intermediate memory 27 for each spatial point in the examination subject 1. The three-dimensional distribution of the dielectric constant $\epsilon(r)$ in the examination subject is then subsequently available in the intermediate memory 27.

The microwave transmitter 3 is then shut off. The characteristic thermal radiation of the examination subject is then identified by the second microwave reception means 31. The temperature distribution in the examination subject 1 is calculated in the calculating means 29 in accordance with the algorithm described above, using the distribution of the dielectric constant. The result is entered in the memory 45.

In an examination subject 1 in whom a tumor or other diseased tissue is to be destroyed by thermal decomposition, temperature elevation of the prescribed volume of the examination subject 1 follows. For this purpose, the heating source 51 is energized for a defined timespan. Subsequently, the characteristic radiation in the examination subject 1 is again detected by the second microwave reception means 31 and is processed to form a three-dimensional temperature distribution, in combination with the distribution of the dielectric constant ϵ(r) which is still available in the intermediate memory 27. Heating of a localized area of the examination subject 1 is then undertaken from the new temperature distribution.

Alternatively, it is possible to first re-activate the microwave transmitter 3 and measure a new distribution of the dielectric constant ϵ(r) by the first reception means 5. The characteristic radiation is then identified and the new temperature distribution is calculated. This operation can be repeated until the critical temperature of about 43° C. for the tissue is reached. This method of temperature identification can be utilized for monitoring the hyperthermia treatment. The frequency of the heating source 51 should be selected so as to be outside of the bandwidth of the frequencies of the first and second reception means 5 and 31.

Although modifications and changes may be suggested by those skilled in the art it is the intention of the inventors to embody within the patent warranted hereon all changes and modifications as reasonably and properly come within the scope of their contribution to the art.

We claim as our invention:

1. A method for non-contacting identification of a three-dimensional temperature distribution in a patient comprising the steps of:
   subjecting said patient to microwave radiation having a phase and amplitude from a microwave source;
   detecting the three-dimensional phase and amplitude of microwave radiation attenuated by said patient;
   computing the three-dimensional dielectric constant distribution in said patient from the detecting three-dimensional phase and amplitude values;
   computing the characteristic thermal radiation of a selected location of said patient from selected phase and amplitude values of microwave radiation attenuated by said patient; and
   computing the three-dimensional temperature distribution of said patient from said three-dimensional dielectric constant distribution and said characteristic thermal radiation of said selected location.

2. A method as claimed in claim 1, wherein the step of computing the three-dimensional temperature distribution of said patient is further defined by solving in a computer an integral equation which expresses said characteristic radiation in terms of at least said temperature distribution and said three-dimensional distribution of the dielectric constant.

3. A method as claimed in claim 1, wherein the step of computing the three-dimensional temperature distribution of said patient is further defined by solving in a computer the following integral equation for the temperature distribution:

$$S(\underline{r}) \propto d_3 r' \epsilon(\underline{r}') \cdot T(\underline{r}') \cdot G(\underline{r} - \underline{r}')$$

wherein $S(\underline{r})$ is the characteristic radiation from said source at a location $\underline{r}$, $\epsilon(\underline{r}')$ is the three-dimensional dielectric constant distribution at a location $\underline{r}'$ in said patient, $T(\underline{r}')$ is the three-dimensional temperature distribution at said location $r'$ and $G(\underline{r} - \underline{r}')$ is Green's function.

4. A method as claimed in claim 1, comprising the additional step of:
heating a localized volume of said patient.

5. A method as claimed in claim 4, wherein said step of heating is undertaken before the step of computing said three-dimensional dielectric constant distribution in said patient.

6. A method as claimed in claim 4, wherein the step of heating is further defined by heating a localized area of said patient to a temperature between 42° and 43° C.

7. A method as claimed in claim 4, comprising the additional steps of:
   superimposing a coordinate system on said patient;
   identifying the location of maximum temperature in said patient in said coordinate system; and
   selecting said localized area for the application of heat in said patient to coincide with the location of said maximum temperature in said coordinate system.

8. A method as claimed in claim 7, wherein the step of superimposing a coordinate system comprises the steps of:
   generating a computer tomograph exposure of said patient; and superimposing said coordinate system on said computer tomograph exposure.

9. A method as claimed in claim 7, wherein the step of superimposing a coordinate system comprises the steps of:
   generating an NMR exposure of said patient; and
   superimposing said coordinate system on said NMR exposure.

10. A method as claimed in claim 1, wherein the step of detecting the three-dimensional phase and amplitude the three-dimensional of microwave radiation attenuated by said patient is further defined by detecting separate sets of the three-dimensional phase and amplitude microwave radiation attenuated by said patient in separate microwave receivers, and wherein said sets of phase and amplitude are respectively separately simultaneously used as said phase and amplitude values in said steps of computing the three-dimensional dielectric constant distribution and computing the characteristic thermal radiation.

11. A method as claimed in claim 1, wherein the step of detecting the three-dimensional phase and amplitude of microwave radiation attenuated by said patient is further defined by sequentially detecting separate sets of said phase and amplitude using a single microwave detector, and sequentially using said sets of phase and amplitude as said phase and amplitude values in said steps of calculating the three-dimensional dielectric constant distribution and calculating the characteristic thermal radiation.

12. A method as claimed in claim 11, wherein the steps of computing the three-dimensional dielectric constant distribution and the step of computing the characteristic thermal radiation are conducted in a single computer, switching between programs for each of said computing steps.

13. An apparatus for non-contacting identification of a three-dimensional temperature distribution in a patient subject comprising:
   means for subjecting said patient to microwave radiation having a phase and amplitude from a microwave source microwave radiation;
   means for detecting the three-dimensional phase and amplitude values of microwave radiation from said microwave source attenuated by said patient;
   means for computing the three-dimensional dielectric constant distribution in said patient from the three-dimensional phase and amplitude values detected by said means for detecting;

means for computing the characteristic thermal radiation of a selected location of said patient from selected ones of the phase and amplitude values detected by said means for detecting; and means for computing the three-dimensional dielectric distribution of said patient from said three-dimensional characteristic thermal radiation of a selected location of said patient.

14. An apparatus as claimed in claim 13, wherein said means for detecting the three-dimensional phase and amplitude of microwave radiation attenuated by said patient comprises first and second microwave receivers.

15. An apparatus as claimed in claim 14, further comprising means for tuning each of said first and second microwave receivers to respectively different frequencies.

16. An apparatus as claimed in claim 15, wherein said means for tuning tunes said first and second microwave receivers to respective for frequencies between about 0.1 and about 10 GHz.

17. An apparatus as claimed in claim 13, further comprising a memory connected to said means for computing the three-dimensional distribution of said dielectric constant for storing the result of the computation therein, and connected to said means for computing the three-dimensional temperature distribution for supplying the result of said three-dimensional dielectric constant distribution computation to said means for computing the three-dimensional temperature distribution.

18. An apparatus as claimed in claim 13, further comprising means disposed relative to said patient for heating a portion of said patient.

19. An apparatus as claimed in claim 18, further comprising control means connected to said means for heating and to said means for computing the three-dimensional temperature distribution for ceasing heating of said portion of said patient by said means for heating when a maximum of the temperature distribution identified by said means for computing the three-dimensional temperature distribution exceeds a selected limit.

20. An apparatus as claimed in claim 19, wherein said selected limit is approximately 43° C.

21. An apparatus as claimed in claim 18, further comprising:

means for superimposing a coordinate system on said patient;

means connected to said means for computing the three-dimensional temperature distribution for identifying the location of maximum temperature of the three-dimensional temperature distribution in said patient in said coordinate system; and means for controlling and positioning said means for heating for directing heat to said patient at the location of said maximum temperature in said coordinate system.

22. An apparatus as claimed in claim 18, wherein said means for heating is a radiation source having a radiation frequency outside of the bandwidth of frequency of said means for reception.

23. An apparatus as claimed in claim 13, further comprising means for ceasing subjecting said patient to microwave radiation by said means for subjecting said patient to microwave radiation during the time when said selected phase and amplitude values of microwave radiation used by said means for computing the characteristic thermal radiation of a selected location of said patient are detected.

* * * * *